US012016405B2

(12) United States Patent
Mazzarolo et al.

(10) Patent No.: US 12,016,405 B2
(45) Date of Patent: Jun. 25, 2024

(54) PATELLA PROTECTION SYSTEM AND KNEE BRACE COMPRISING SUCH A PATELLA PROTECTION SYSTEM

(71) Applicant: Alpinestars Research S.p.A., Maser (IT)

(72) Inventors: Giovanni Mazzarolo, Coste di Maser (IT); Sebastian Hess, Schorndorf (DE)

(73) Assignee: ALPINESTARS RESEARCH S.P.A., Maser (IT)

( * ) Notice: Subject to any disclaimer, the term of this patent is extended or adjusted under 35 U.S.C. 154(b) by 366 days.

(21) Appl. No.: 17/270,310

(22) PCT Filed: Aug. 21, 2019

(86) PCT No.: PCT/EP2019/072347
§ 371 (c)(1),
(2) Date: Feb. 22, 2021

(87) PCT Pub. No.: WO2020/038987
PCT Pub. Date: Feb. 27, 2020

(65) Prior Publication Data
US 2021/0195969 A1    Jul. 1, 2021

(30) Foreign Application Priority Data

Aug. 23, 2018  (IT) .................. 102018000008174

(51) Int. Cl.
*A41D 13/06* (2006.01)
*A61F 5/01* (2006.01)
*A63B 71/12* (2006.01)

(52) U.S. Cl.
CPC .......... *A41D 13/065* (2013.01); *A61F 5/0123* (2013.01); *A61F 2005/0141* (2013.01);
(Continued)

(58) Field of Classification Search
CPC ............ A61F 5/0123; A61F 2005/0176; A61F 2005/0141; A61F 2005/0165;
(Continued)

(56) References Cited

U.S. PATENT DOCUMENTS 2,587,166 A * 2/1952 Jovick ................... A61F 5/0125
125/11.17
4,068,312 A * 1/1978 Ledesma .............. A41D 13/065
2/24
(Continued)

FOREIGN PATENT DOCUMENTS

DE       3626005 A1    2/1988
SE       517 201   *  5/2002  ............. A63B 71/12
(Continued)

OTHER PUBLICATIONS

Lars, Eghamn, Joint appliance Persue Shinguard, May 7, 2002.*
(Continued)

*Primary Examiner* — Camtu T Nguyen
(74) *Attorney, Agent, or Firm* — Fredrikson & Byron, P.A.

(57) ABSTRACT

A patella protection system, and a knee brace including such a patella protection system. The patella protection system including an upper member to be positioned in proximity of an upper part of the wearer's leg, a lower member to be positioned in proximity of a lower part of the wearer's leg and an intermediate guard member to be positioned over the patella and operatively connected to the upper member and the lower member. The upper member and the lower member are designed to move within the intermediate guard member between a straight configuration and an angled/angulated configuration.

19 Claims, 11 Drawing Sheets

(52) U.S. Cl.
CPC ........... *A61F 2005/0165* (2013.01); *A61F 2005/0176* (2013.01); *A63B 2071/125* (2013.01)

(58) Field of Classification Search
CPC A63B 2071/125; A41D 13/065; A41D 13/06; A41D 13/0556; A41D 13/0568; A41D 13/05
See application file for complete search history.

(56) References Cited

U.S. PATENT DOCUMENTS

| | | | | |
|---|---|---|---|---|
| 4,409,689 | A * | 10/1983 | Buring | A63B 71/1225 2/22 |
| 4,599,748 | A * | 7/1986 | Garcia | A61F 5/0123 2/24 |
| 6,789,264 | B2 * | 9/2004 | Budda | A63B 71/1225 2/22 |
| 8,048,013 | B2 * | 11/2011 | Ingimundarson | A61F 5/0123 602/26 |
| 10,420,668 | B2 * | 9/2019 | Klutts | A61F 5/0106 |
| 2002/0107462 | A1 * | 8/2002 | Freeman | A61F 5/0123 602/16 |
| 2006/0167396 | A1 * | 7/2006 | Berger | A63B 71/1225 602/5 |
| 2008/0195013 | A1 * | 8/2008 | Ingimundarson | A61F 5/0123 602/26 |
| 2011/0098618 | A1 * | 4/2011 | Fleming | A61F 5/0123 602/26 |

FOREIGN PATENT DOCUMENTS

| | | |
|---|---|---|
| WO | 9418916 A1 | 9/1994 |
| WO | 02066122 A1 | 8/2002 |

OTHER PUBLICATIONS

PCT International Search Report and Written Opinion dated Sep. 10, 2019 for Intl. App. No. PCT/EP2019/072347, from which the instant application is based, 11 pgs.

* cited by examiner

PATELLA PROTECTION SYSTEM AND KNEE BRACE COMPRISING SUCH A PATELLA PROTECTION SYSTEM

RELATED APPLICATIONS

This application is a 35 U.S.C. 371 national stage filing from International Application No. PCT/EP2019/072347, filed Aug. 21, 2019, which claims priority to Italian Application No. 102018000008174, filed Aug. 23, 2018, the teachings of which are incorporated herein by reference.

FIELD OF THE INVENTION

The present invention relates to a patella protection system designed to be worn by a user. Moreover, the present invention relates to a knee brace designed to be worn by a user and comprising such a patella protection system.

BACKGROUND

In the technical field of wearable protection systems, orthopaedic protection systems are well known and are designed to protect a wearer's body part from injuries, particularly during physical activity.

Examples of such systems are the braces for protecting the knees of wearers, in particular during motorcycle racing and skiing.

In general, knee braces are used to limit the movement of the knee joint within a predetermined angular range, thus avoiding ligament tears, hypertension or other injuries.

These kinds of braces usually comprise an upper frame member, i.e. the member that is fastened to and protects the upper part of the leg of the wearer, a lower frame member, i.e. the member that is fastened to and protects the lower part of the leg of the wearer, and an intermediate guard member positioned between the upper frame and lower frame members. In the following, the expression "upper part of the leg" will indicate the part of leg comprised between the patella and the waist of the user, while the expression "lower part of the leg" will indicate the part of the leg comprised between the patella and the foot of the user.

The upper and the lower frame members are pivotally connected therebetween and with the intermediate member to allow the brace to move between a straight configuration and an angulated configuration, when the user flexes his/her leg.

A major drawback of these solutions consists in that the upper and lower frame members are distanced from the intermediate member when the brace is flexed, thus rendering the patella exposed and vulnerable to injuries.

Thus, these knee braces do not provide an effective and continuous protection of the patella during the movement of the members between the straight configuration and the angulated configuration of the brace.

In order to partially overcome this drawback, there are provided knee braces which allow for a more efficient protection of the patella in all the operative configurations.

U.S. Pat. No. 9,693,887 describes a protective patella guard adapted for use with a knee brace having upper and lower frame members. The protective patella guard includes an upper cup element coupled to the upper frame member, a lower cup element coupled to the lower frame member and an intermediate cup member operatively coupled to the upper cup element.

All elements of the patella guard are formed by concave cups. The patella guard is transitional between a first (straight) configuration and a second (angulated) configuration, wherein the degree of overlap between the upper cup element, the lower cup element and the intermediate cup element decreases as the patella guard transitions from the first configuration to the second configuration.

Even if this kind of protection system manages to solve some of the above mentioned technical problems, it has further drawbacks.

A first drawback lies in that the upper and lower cup elements could laterally move or block during configuration transitions, thus preventing the correct functioning of the brace.

A further drawback concerns the fact that this system does not allow an effective breathability of the user's leg, since the cup elements have a closed wall.

Another drawback is that the intermediate cup element has a reduced deformability and doesn't allow an efficient absorption of the strikes and blows against the brace.

Yet another drawback lies in that the upper and the lower cup elements are made of a rigid material and could not be deformed at all during configuration transition, thus preventing the adaptation of the system over the user's leg.

A further drawback is that the hinge means of the brace which connect the upper and the lower frame members do not accurately block the rotation thereof within a predetermined angular range.

BRIEF SUMMARIES OF OBJECTS OF THE INVENTION

An object of the present invention is to provide a patella protection system for use with a knee brace which allow to solve the above mentioned drawbacks.

In particular, an aim of the present invention is to provide a patella protection system which allows the protection of the patella during the movement from a straight configuration to an angulated configuration.

Moreover, a further aim of the present invention is to provide a patella protection system which allows movement from a straight configuration to an angulated configuration without blockings or drifting.

Yet another aim of the present invention is to provide a patella protection system which allows the breathability of the user's leg in use.

A further aim of the present invention is to provide a patella protection system wherein an intermediate guard member could deform and better absorb blows and strikes.

Another aim of the present invention is to provide a patella protection system that can adapt to the user's leg during movement from a straight configuration to an angulated configuration.

A further aim of the present invention is to provide a knee brace which allows to limit the rotation of the frame members within a predetermined angular range.

These and other objects and aims are achieved by a patella protection system as claimed in claim 1 and by a knee brace as claimed in claim 16.

BRIEF DESCRIPTIONS OF THE DRAWINGS

The advantages and the characteristic features of the invention will appear more clearly from the following description of a preferred, but not exclusive, embodiment of a patella protection system with reference to the accompanying figures in which.

DETAILED DESCRIPTION OF EMBODIMENTS OF THE INVENTION

Figure 1:
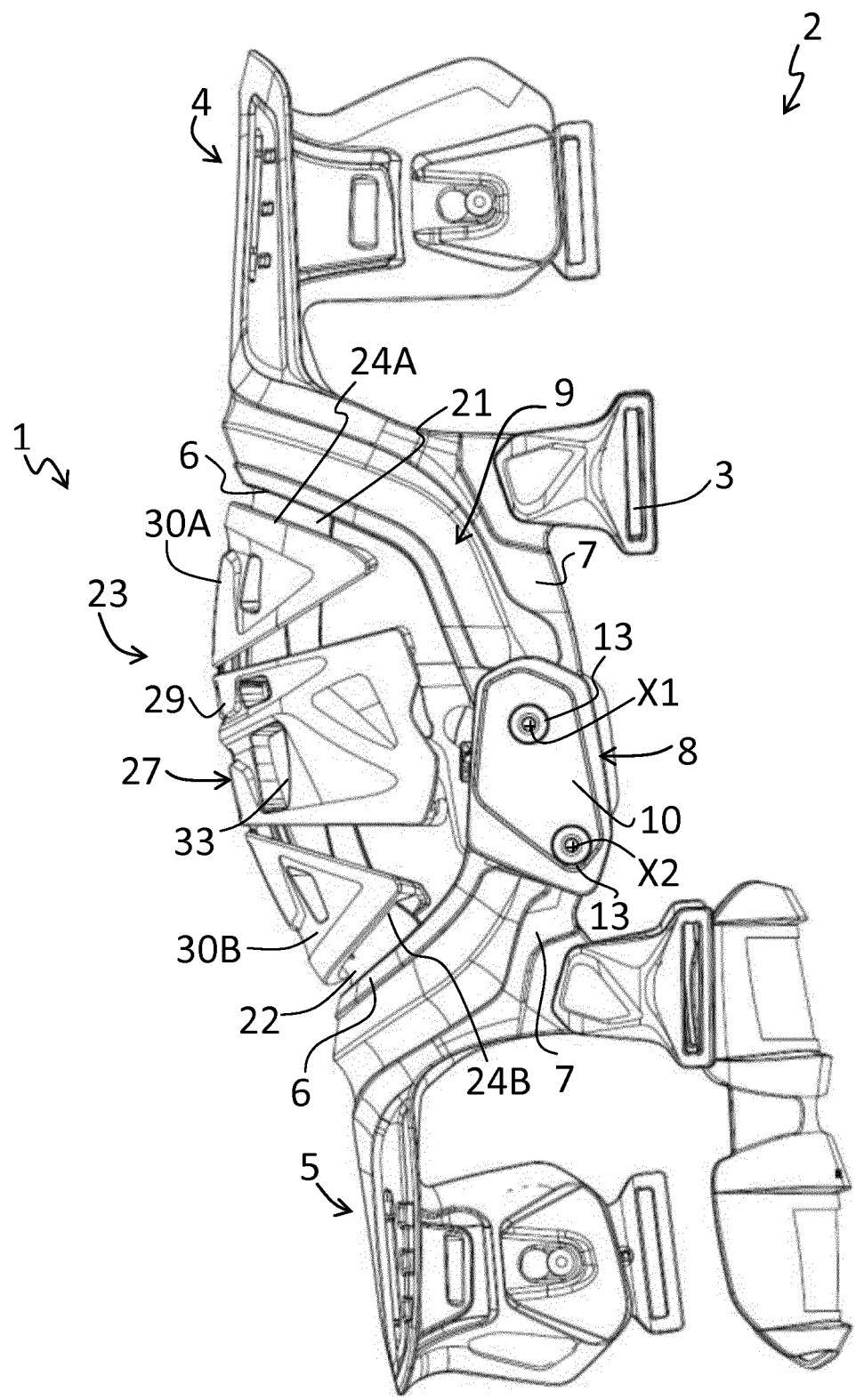
FIG. 1 shows a side view of the knee brace of the present invention with the patella protection system in a first operative configuration.

With reference to the attached figures, a patella protection system, indicated as a whole by the reference 1, and a knee brace, indicated as a whole by the reference 2, are disclosed. The patella protection system 1 and the knee brace 2 are suitable for being used by motorcyclists, preferably by motocross riders, but they could also be used by skiers or in other fields where an effective protection of the user's leg must be obtained.

Preferably, the knee brace 2 could be worn by the user underneath a leather suit, not shown in the figures, and fastened to a leg of the user, also not shown in the figures, by suitable securing means 3.

Such securing means 3 can comprise, for example, buckles for the insertion and the securement of strips or bands, not shown in the figures. In alternative, the securing means 3 could also comprise tear-strip means without prejudice to the scope of the protection of the present invention.

As already known, the knee brace 2 comprises an upper frame member 4 and a lower frame member 5 which are designed to be positioned and fastened at the upper part and at the lower part of the wearer's leg respectively.

Figure 1A:
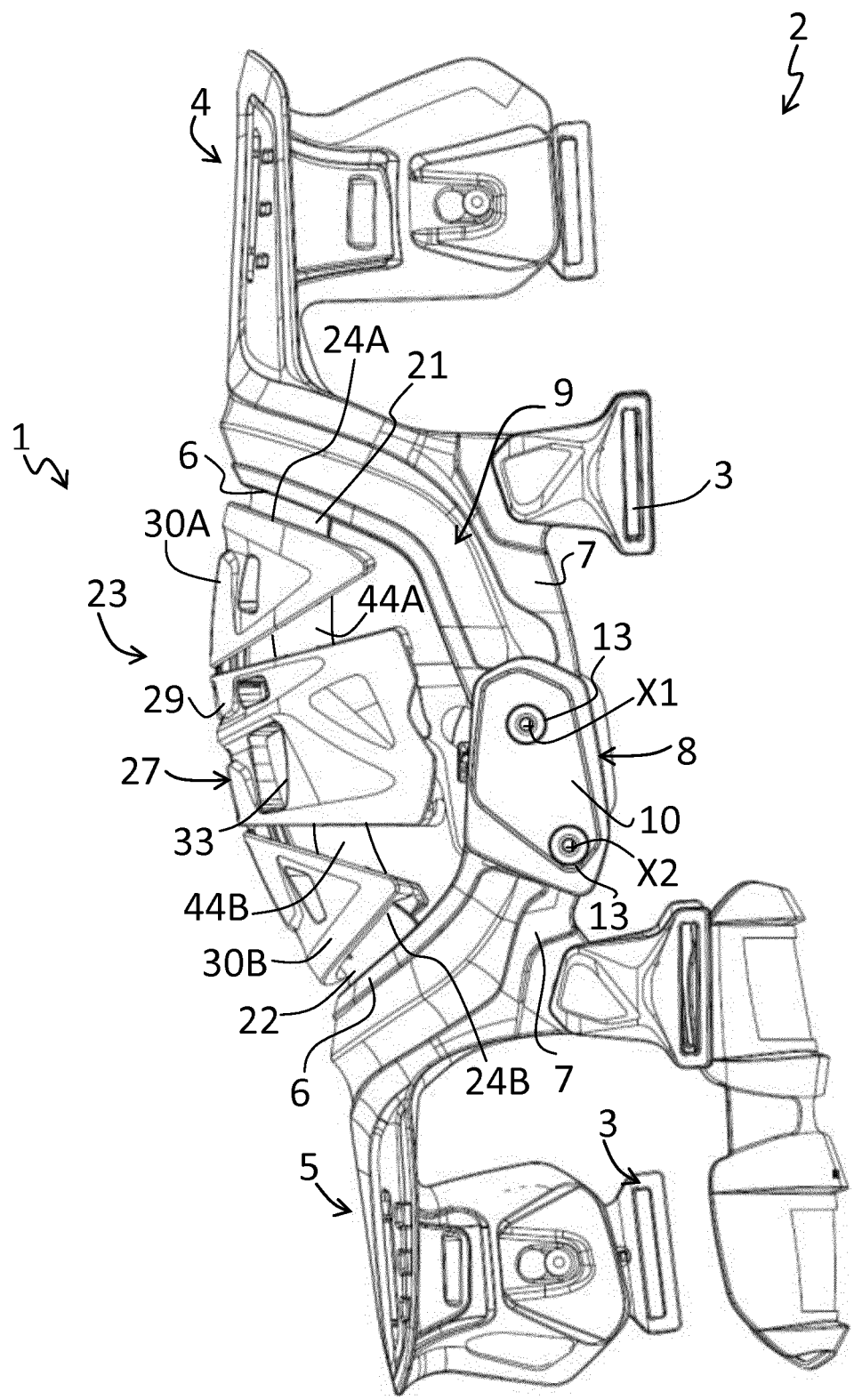
FIG. 1a shows a view similar to FIG. 1, but referring to a different embodiment.
Figure 2:
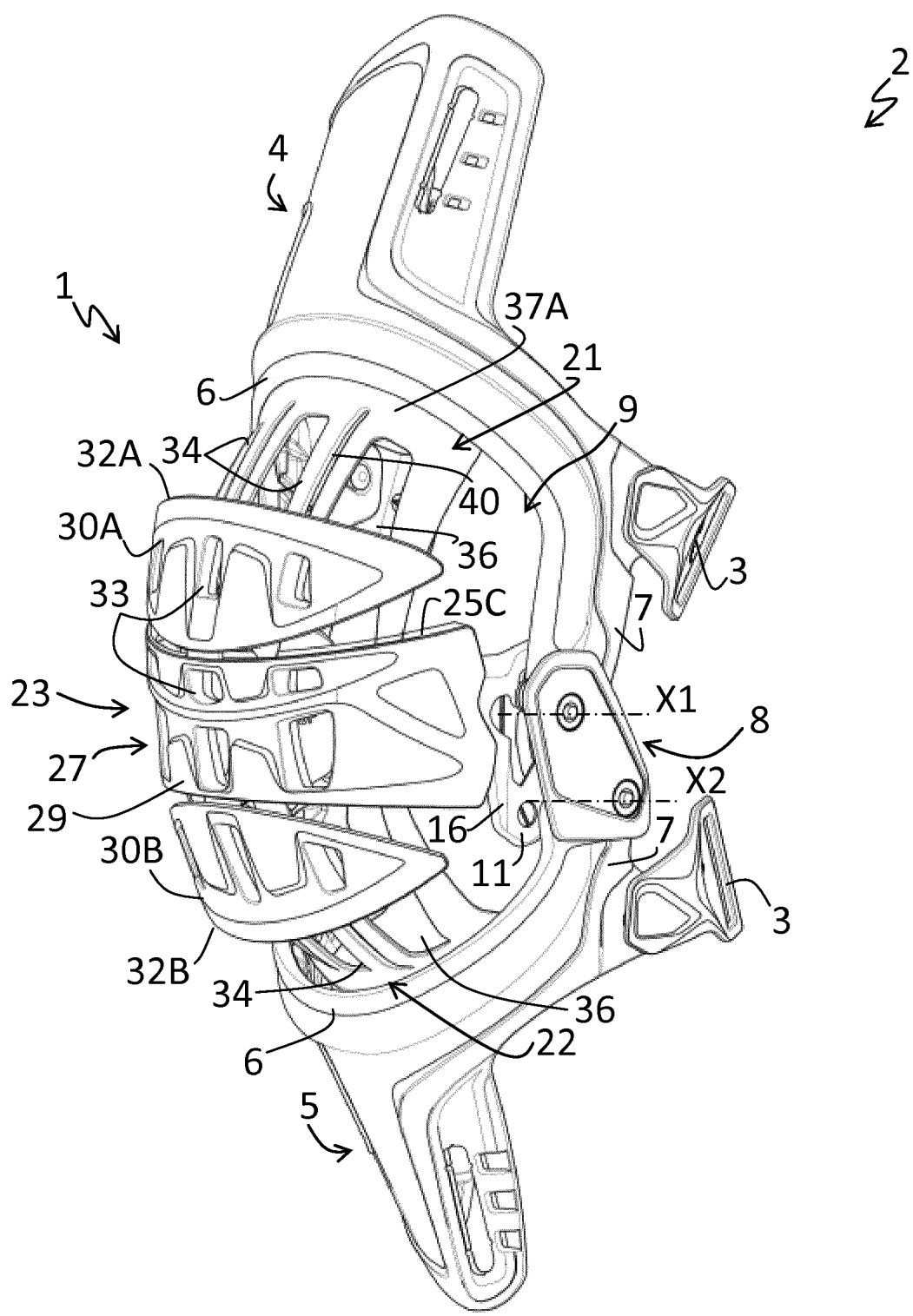
FIG. 2 shows a perspective view of the knee brace of the present invention with the patella protection system in a second operative configuration.

For these reasons, as shown in FIGS. 1, 1a and 2, securing means 3 are connected to the upper and the lower frame members 4, 5.

Advantageously, the upper frame member 4 and the lower frame member 5 can be made of a rigid polymeric material, eventually mixed with carbon, and have a shape corresponding to the shape of the upper and the lower parts of the leg.

The upper and the lower frame members 4, 5 may also be formed of different polymeric material, without prejudice to the scope of protection of the present invention.

The upper frame member 4 and the lower frame member 5 can be internally covered with a layer of a soft material, not shown in the figures, which is advantageously suitable to improve impact absorption.

Further, the knee brace 2 comprises the patella protection system 1, which is interposed between the upper frame member 4 and the lower frame member 5 and it is operatively connected thereto. When in use, the patella protection system 1 is designed to be positioned over the patella of the user.

The upper frame member 4 and the lower frame member 5 are pivotally connected therebetween and with the patella protection system 1 in order to rotate about respective rotation axes X1, X2, as shown in FIGS. 1, 1a and 2, within a predetermined angular range relative to the patella protection system 1 when the leg is flexed.

In particular, both the upper frame member 4 and the lower frame member 5 comprise a central edge portion 6 and a pair of side brackets 7 pivotally connected with the side brackets 7 of the other member by suitable hinge means 8, better illustrated in FIGS. 1, 1a, 2, 7, 9, 10, 12 and 13.

Preferably, the hinge means 8 are of the four-pivot type in order for each of the upper member 4 and the lower member 5 to rotate about respective rotation axes X1, X2, as shown in FIGS. 1, 1a and 2.

Once connected, the side brackets 7 and the central edge portion 6 of both the upper frame member 4 and the lower frame member 5 delimit a central space 9 for the housing of the patella protection system 1. The hinge means 8 are positioned at both the sides of the central space 9.

Figure 12:
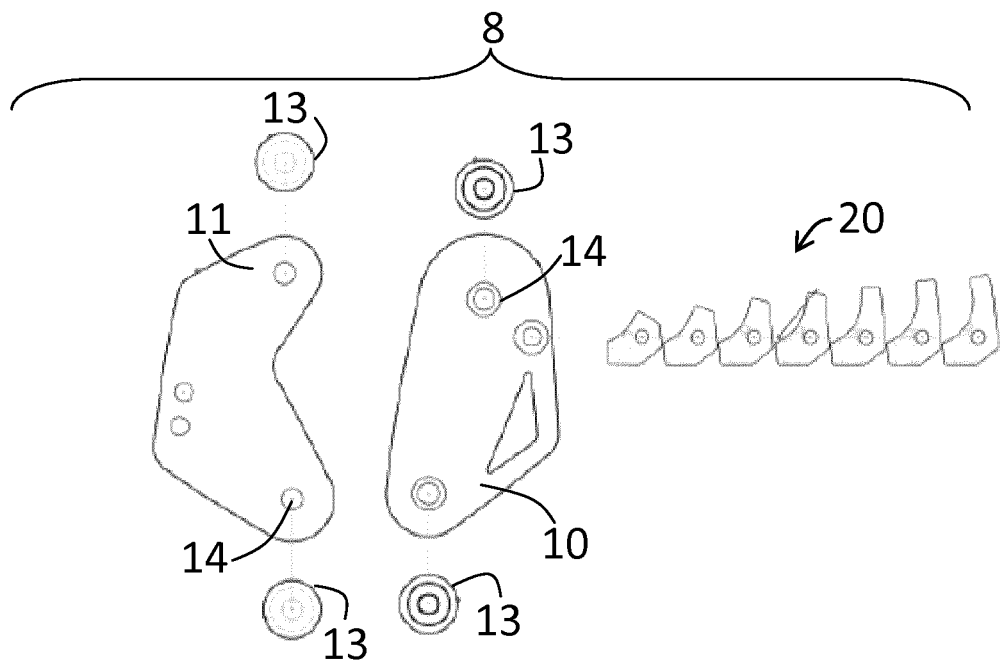
FIG. 12 is an exploded front view of the hinge means of the knee brace.

Preferably, each of the hinge means 8 comprises an outer plate 10 and an inner plate 11 defining an interspace 12 and coupled by at least two rivets 13 inserted in respective through holes 14. Thus, each of the plates 10, 11 comprises two through holes 14, as shown in FIG. 12.

Figure 13:
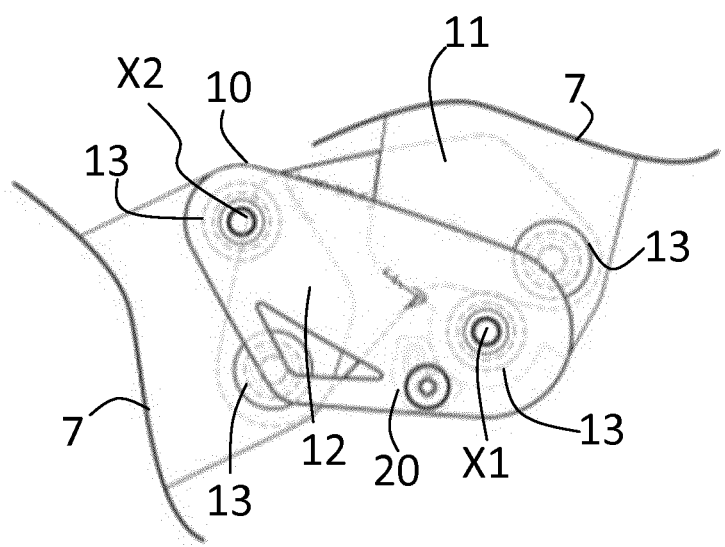
FIG. 13 is a schematic side view of a part of the upper and lower members of the knee brace coupled by the hinge means.

The ends of the side brackets 7 are inserted in the interspace 12 and comprise through holes 15 (see FIGS. 7 and 10) designed to be aligned with the holes 14 of the plates 10, 11 for the insertion of the rivets 13, as better shown in FIG. 13.

Thus, the rivets 13 define the rotation axes X1, X2 of the upper frame member 4 and lower frame member 5.

The surface of the inner plate 11 oriented towards the space 9 may be covered with a layer of protection soft material, not shown in the figures, for protecting the knee on both its sides and avoiding injuries.

Advantageously, the inner plates 11 of the hinge means 8 comprise flanges 16 (see FIGS. 11 and 11a) secured to patella protection system 1 on both its sides. In particular, each of the flanges 16 can comprise a respective slot 17 for the insertion of a connection pin 18 formed on the protection system 1, as better illustrated in FIGS. 4 and 9. In FIGS. 12 and 13 the inner plate 11 is shown schematically without the flange 16.

Each connection pin 18 may slide with a limited angular excursion within the slot 17, so as to assure a certain degree of freedom to the patella protection system 1 relative to the coupled upper frame member 4 and lower frame member 5.

Opportunely, the hinge means 8 can comprise at least one stop member 20 designed to interact with the ends of the side brackets 7 for limiting the rotation of the upper frame member 4 and the lower frame member 5.

In the embodiments shown in the figures, in particular FIGS. 12 and 13, there is provided one stop member 20 for each of the hinge means 8.

The stop member 20 is positioned in the interspace 12 and may be secured to the inner surface of the inner plate 11 or the outer plate 10. The stop member 20 may be chosen among a set of stop members having different sizes and shapes (see FIG. 12).

The user will select the stop member with the desired size in order to settle the angular range within which the upper frame member 4 and the lower frame member 5 can rotate.

In the following a preferred embodiment of the patella protection system 1 will be described with reference to the components of the knee brace 2 described above.

Preferably, the patella protection system 1 comprises an upper member 21, designed to be positioned in proximity of the upper part of the wearer's leg, and a lower member 22, designed to be positioned in proximity of the lower part of the wearer's leg. The upper member 21 and the lower member 22 may have the same configuration, as shown in the figures.

The patella protection system 1 further comprises an intermediate guard member 23 designed to be positioned over the patella and to be operatively connected to the upper member 21 and the lower member 22.

The intermediate guard member 23 may have a different shape and configuration with respect to the upper member 21 and the lower member 22, as shown in the figures.

Figure 7:
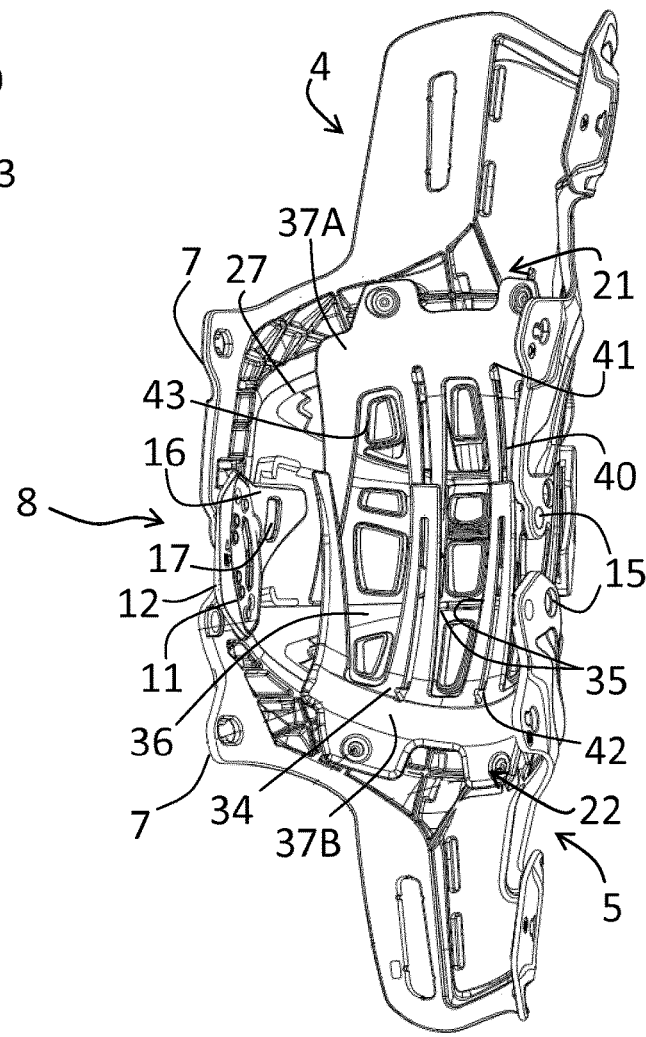
FIG. 7 shows a perspective rear view of the knee brace of FIG. 1 without the inner shell of the intermediate guard member.

The upper member 21 and the lower member 22 are secured, respectively, to the upper frame member 4 and the lower frame member 5 of the knee brace 2, preferably at their central edge portion 6, as shown in FIGS. 2 and 7.

Thus, the upper member 21 and lower member 22 are designed to be connected to the upper and the lower parts of the leg by way of their connection with the upper frame member 4 and the lower frame member 5.

Further, the upper member 21 and the lower member 22 are not directly connected with the hinge means 8 described above, but they are designed to move jointly with the upper frame member 4 and the lower frame member 5 of the knee brace 2.

Figure 9:
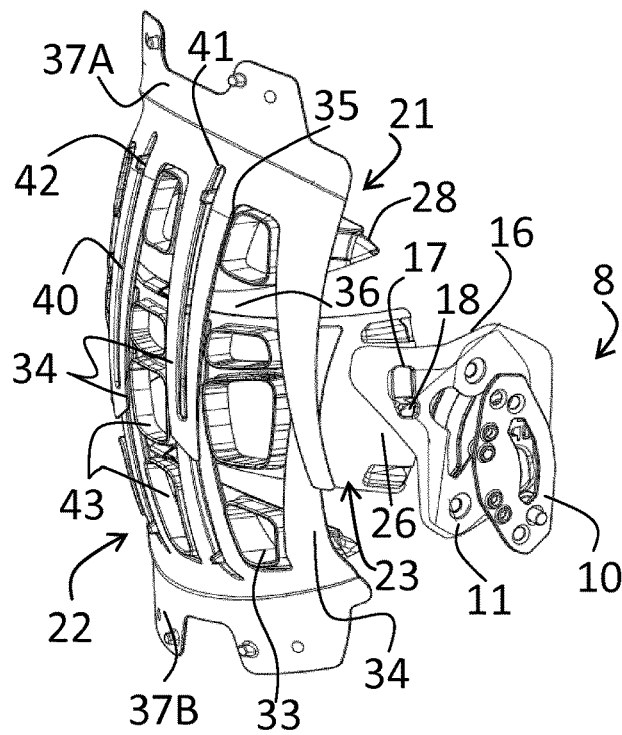
FIG. 9 shows a perspective front view of the patella protection system of the present invention without the front shell of the intermediate guard member.
Figure 10:
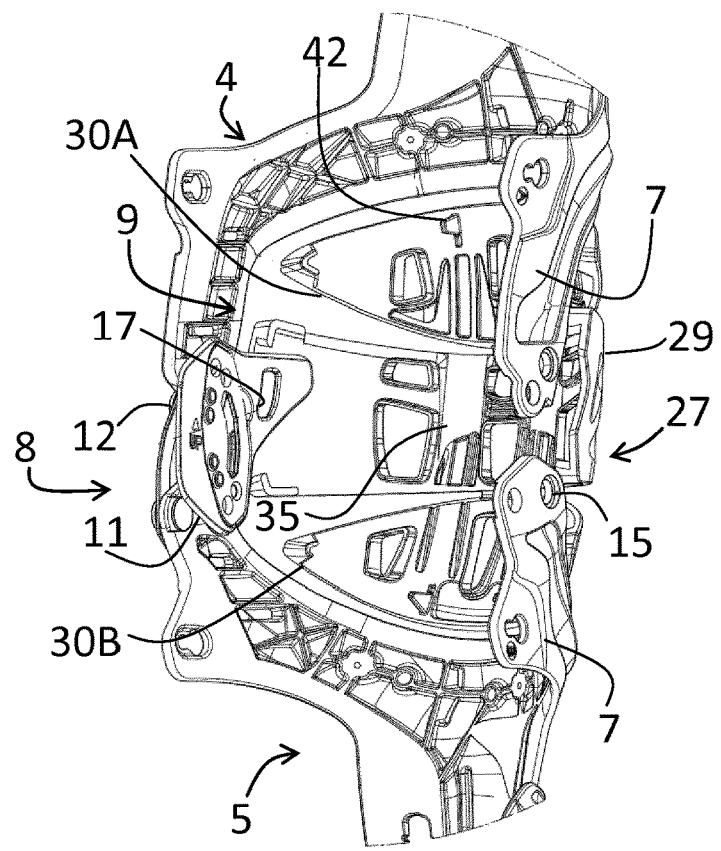
FIG. 10 shows a perspective rear view of the knee brace without the upper and the lower members.

Advantageously, the intermediate guard member 23 is connected to the hinge means 8, namely it comprises, at both its sides, the respective connection pin 18, as described above, inserted in the slot 17 of a respective flange 16, as better shown in FIG. 9.

In this regard, it can be seen from the figures that the upper member 21 and the lower member 22 are designed to move, jointly with the upper frame member 4 and the lower frame member 5, within the intermediate guard member 23.

Figure 3:
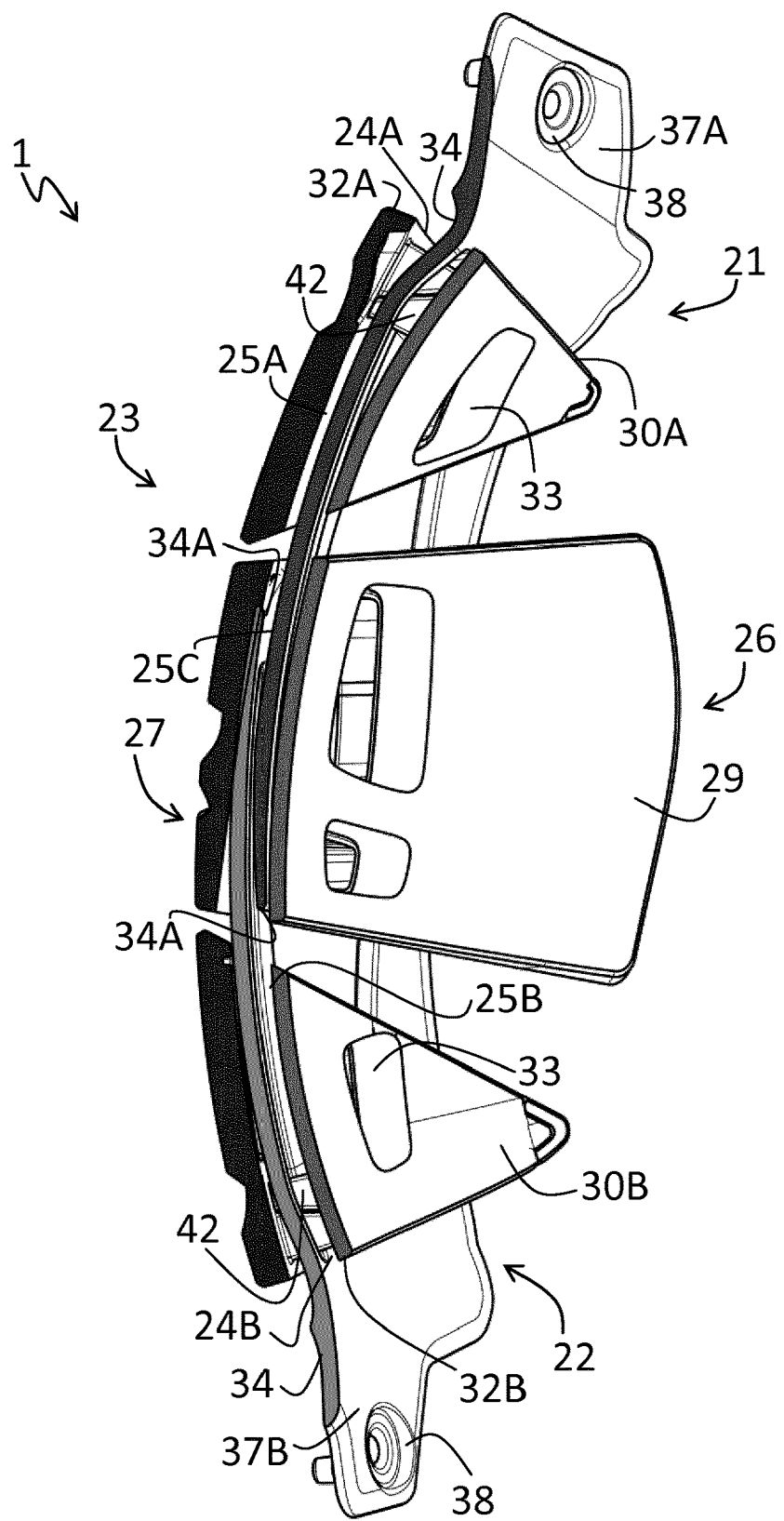
FIG. 3 shows a longitudinal sectioned view of a particular of the patella protection system in the first operative configuration, as illustrated in FIG. 1.
Figure 4:
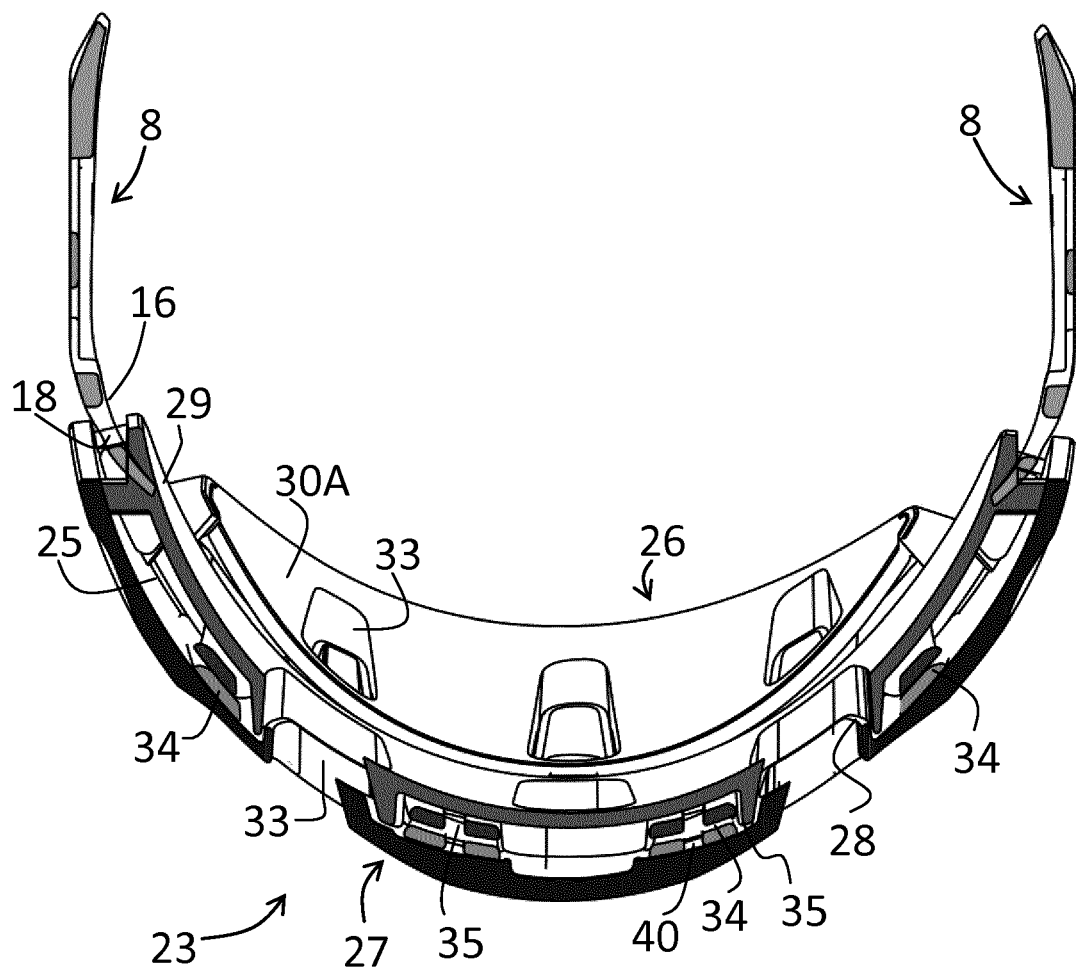
FIG. 4 shows a transverse sectioned view of a particular of the patella protection system in the second operative configuration, as illustrated in FIG. 2.
Figure 5:
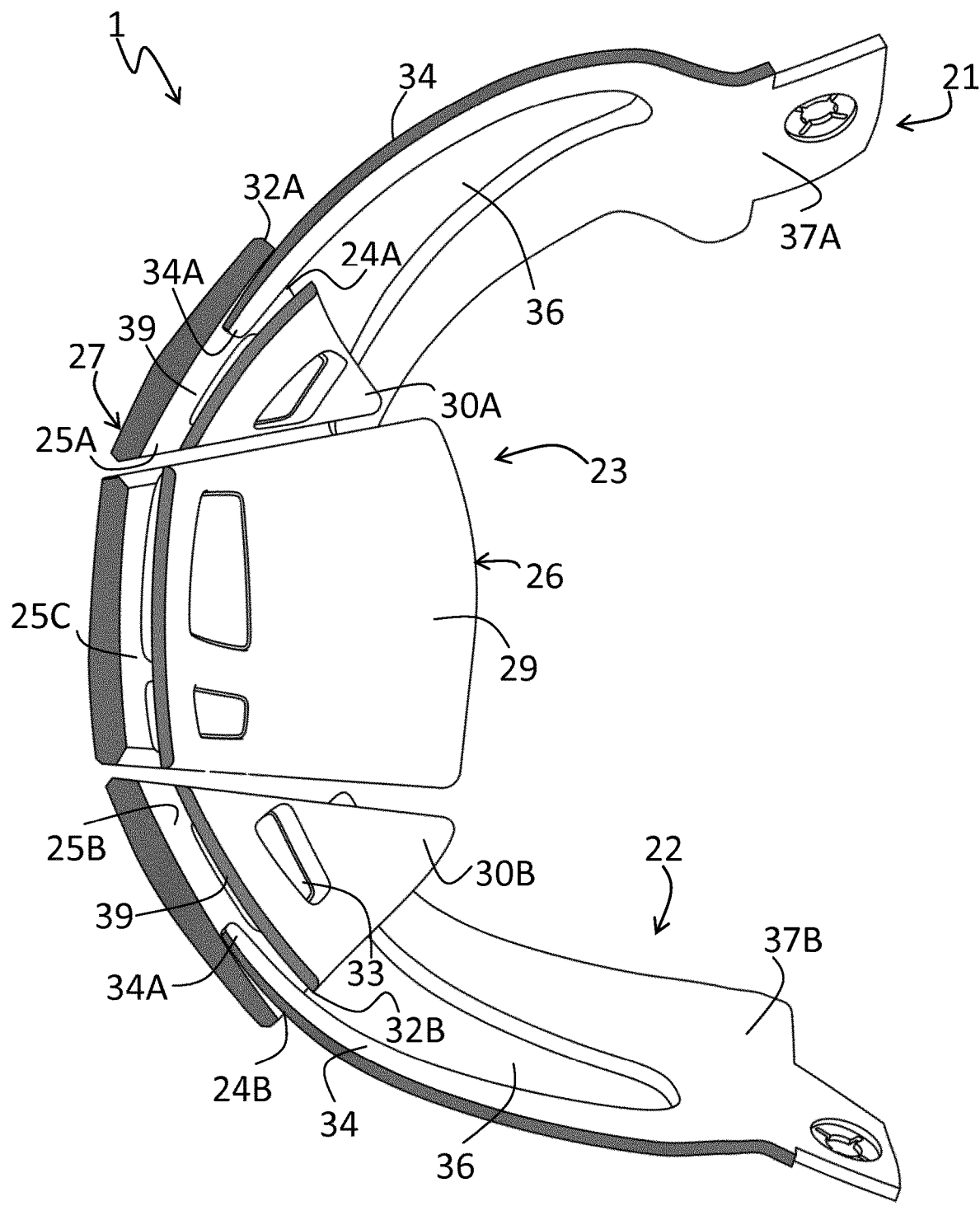
FIG. 5 shows a longitudinal sectioned view of a particular of the patella protection system in the second operative configuration, as illustrated in FIG. 2.

In particular, the upper member 21 and the lower member 22 move between a straight configuration, better illustrated in FIGS. 1, 1a and 3, and an angulated configuration, better illustrated in FIGS. 2, 4 and 5.

The upper member 21 and the lower member 22, as well as the upper frame member 4 and the lower frame member 5, during movement between the straight and angulated configuration, rotate accordingly with the pivoting motion of the knee joint which has to be protected.

The expressions "straight configuration" and "angulated configuration" are well known in the art and they will not be explained further in the present disclosure.

When the upper member 21 and the lower member 22 are in the straight configuration they have a predetermined degree of overlap there between within the intermediate guard member 23, as shown in FIG. 3.

In the angulated configuration the upper member 21 and the lower member 22 have at least a reduced degree of overlap there between within the intermediate guard member 23, as shown in FIG. 5.

By way of comparison to the straight configuration illustrated in FIG. 3, the angled configuration shown in FIG. 5 includes a correspondingly larger angle of deflection between the upper member 21 and the lower member 22. Continuing with FIGS. 3 and 5, the straight configuration can be viewed as having a maximum degree of overlap between said upper member 21 and said lower member 22, while in the angled configuration such degree of overlap is reduced from the maximum degree of overlap. As further shown in FIG. 5, when moved to an angled configuration, the degree of overlap can be reduced to a degree of no overlap.

According to one embodiment of the present invention, the intermediate guard member 23 is a box-like member with end openings 24A, 24B and an inner cavity 25 for the slidable insertion and guidance of the upper member 21 and the lower member 22 during the movement thereof between the straight and the angulated configuration, and vice versa.

In particular, when the patella protection system 1 is in the straight configuration, the upper member 21 and the lower member 22 are inserted in the inner cavity 25 and are positioned over the patella. When the patella protection system 1 is in the angulated configuration the upper member 21 and the lower member 22 occupy the space between the edge portions 6 of the upper frame member 4 and the lower frame member 5 and the intermediate guard member 23.

In this regard, the intermediate guard member 23 of the patella protection system 1 can be formed by a pair of shells 26, 27 coupled there between and designed to delimit the inner cavity 25.

In particular, the intermediate guard member 23 comprises an inner shell 26, which faces the knee of the user when the patella protection system 1 is in use, and an outer shell 27 oriented to the opposite side, as shown in FIGS. 3-5.

It is to be understood that the inner cavity 25 is delimited between the inner surfaces 39 of the inner shell 26 and the outer shell 27, which have a concave shape.

Thus, by saying that the upper member 21 and the lower member 22 have a predetermined degree of overlap within the intermediate guard member 23, it is meant that the upper member 21 and the lower member 22 overlap the inner shell 26, namely its inner surface 39, when they are inserted in the inner cavity 25.

Figure 8:
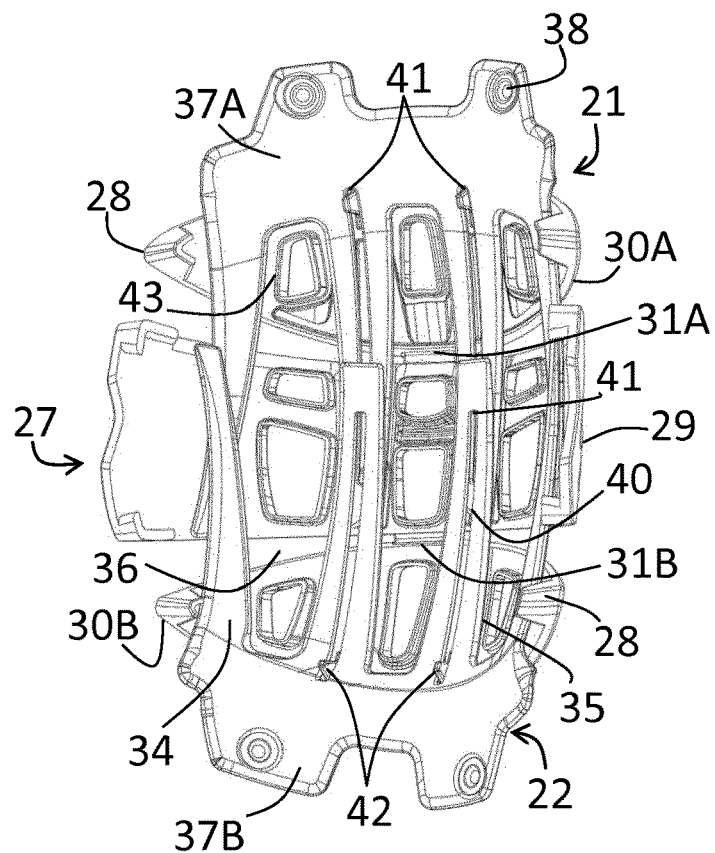
FIG. 8 shows a perspective rear view of the patella protection system of the present invention without the inner shell of the intermediate guard member.

The shells 26, 27, as illustrated in the FIGS. 8 and 9, may be connected by snap-fit connection means 28 or by different types of connection, for example by means of screws, without prejudice to the scope of protection of the present invention. Further, the two shells 26, 27 could also be integrally formed with the inner cavity 25 provided there between.

Advantageously, when the patella protection system 1 is in use, the outer shell 27 remains always exposed outward, both in the straight configuration and in the angulated configuration, since the upper member 21 and the lower member 22 slide inside the inner cavity 25 of the intermediate guard member 23.

Such a configuration allows for an increased absorption of the impacts by deformation of the walls of the shells 26, 27, according with the standard EN 1621-1.

Preferably, the inner shell 26 and the outer shell 27 comprise at least two portions 29, 30A, 30B connected by at least one hinge section 31A, 31B. In particular, as better shown in FIGS. 1, 2, 3, 5 and 11, the inner shell 26 and the outer shell 27 comprise three portions, namely a central portion 29, an upper portion 30A and a lower portion 30B.

The upper portion 30A is the portion proximate to the upper member 21, and the lower portion 30B is the portion proximate to the lower member 22.

The number of portions of the inner shell 26 and the outer shell 27 can also be different, according with the use of the patella protection system 1, without prejudice to the scope of protection of the present invention.

Figure 6:
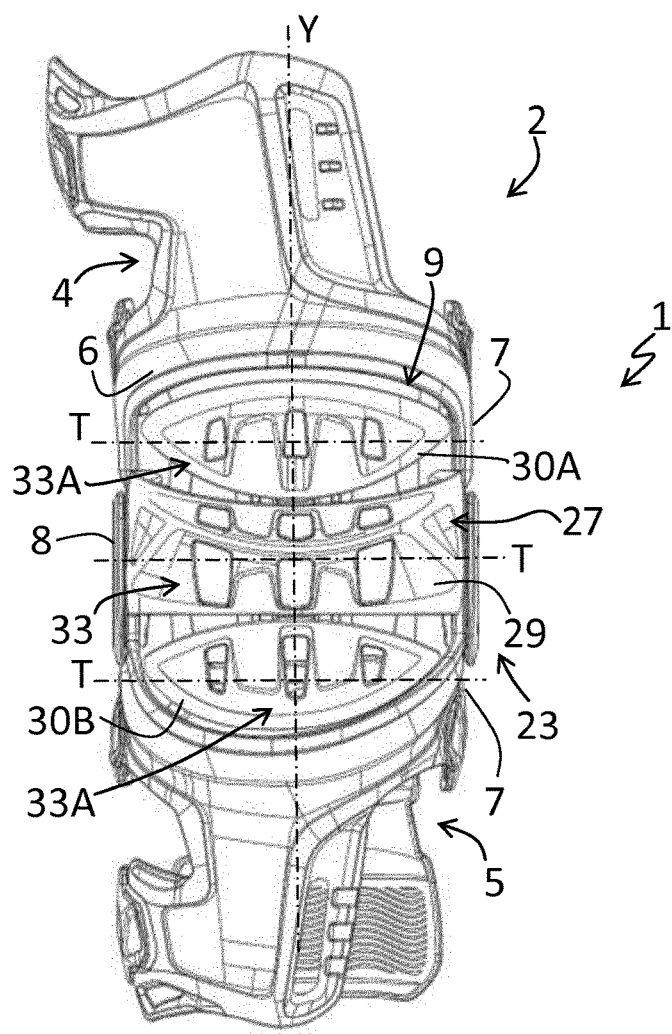
FIG. 6 shows a front view of the knee brace of FIG. 1.

The upper portion 30A and the lower portion 30B are connected to the central portion 29 at a respective hinge section 31A, 31B and all the portions 29, 30A, 30B define transverse extension axes T with reference to an elongated axis Y which corresponds to the extension axis of the leg, as shown in FIG. 6.

Opportunely, each of the shells 26, 27 can be manufactured by injection as a single segmented element so as to define the three portions 29, 30A, 30B connected by the hinge sections 31A, 31B.

The at least one hinge section 31A, 31B has a reduced thickness relative to the shells portions 29, 30A, 30B. In particular, the material of the hinge sections 31A, 31B is the same of the material of the portions 29, 30A, 30B but it has a reduced thickness relative to the material of the portions 29, 30A, 30B.

This configuration allows the improved flexion of the portions of the intermediate guard member 23 and their dynamic adaptation during the movement and the flexion of the knee.

The portions 29, 30A, 30B and the hinge sections 31A, 31B could also be manufactured with different polymeric material and by different processes, without prejudice to the scope of protection of the present invention.

The inner cavity 25 of the intermediate guard member 23 may be segmented as well as the portions 29, 30A, 30B so as to form three parts 25A, 25B, 25C, as shown in FIGS. 3 and 5. Precisely, the parts 25A, 25B, 25C are defined respectively inside the portions 29, 30A, 30B.

The above indicated end openings 24A, 24B can be formed on the transverse ends 32A, 32B of the upper portion 30A and the lower portion 30B which are not connected to the central portion 29, as illustrated in FIGS. 3 and 5.

Further, the central portion 29 of the inner shell 26 can comprise, at both its transverse sides, the connection pin 18 which is designed to be inserted in the slot 17 of the flange 16 of the hinge means 8, as illustrated in FIG. 9.

Preferably, each portion 29, 30A, 30B of the inner shell 26 and the outer shell 27 comprises at least one ventilation hole 33 aligned with the hole of the other shell for allowing the breathability of the knee when the patella protection system 1 is in use.

Figure 11:
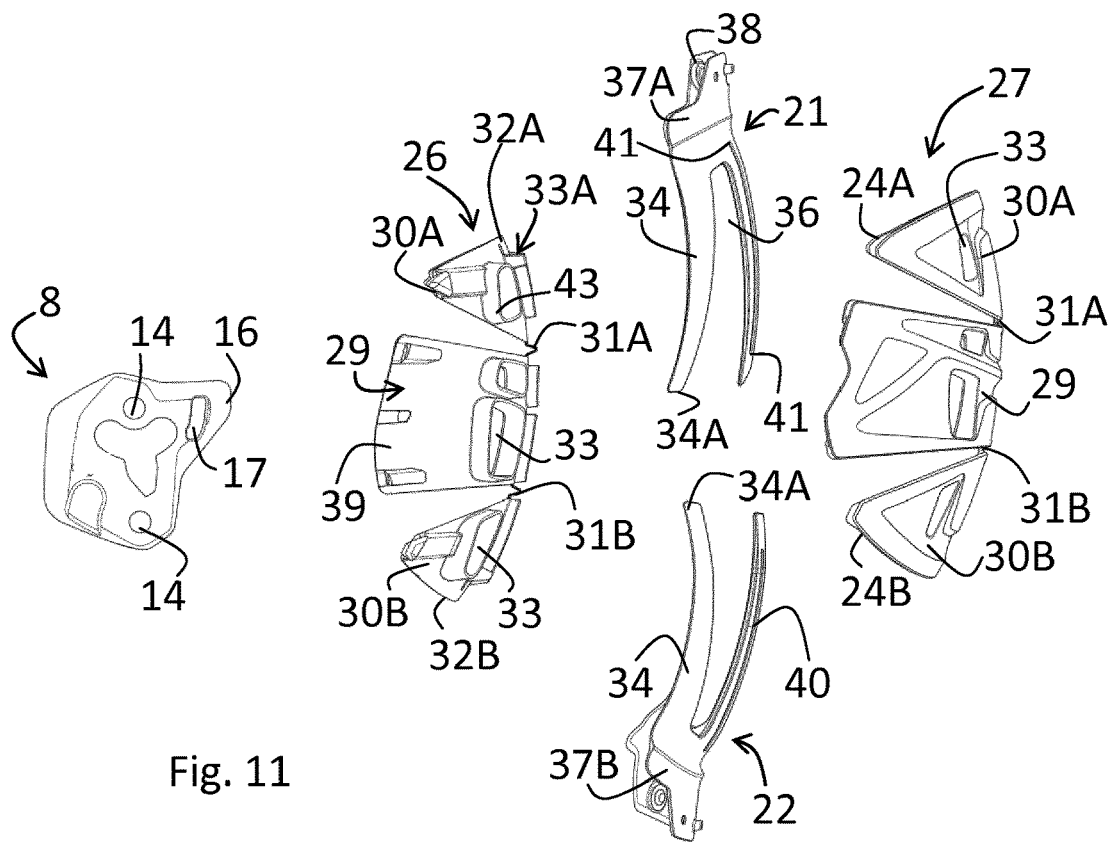
FIG. 11 is an exploded perspective view of the patella protection system in a different configuration with respect to the preceding figures and with an element of the hinge means of the brace.
Figure 11A:
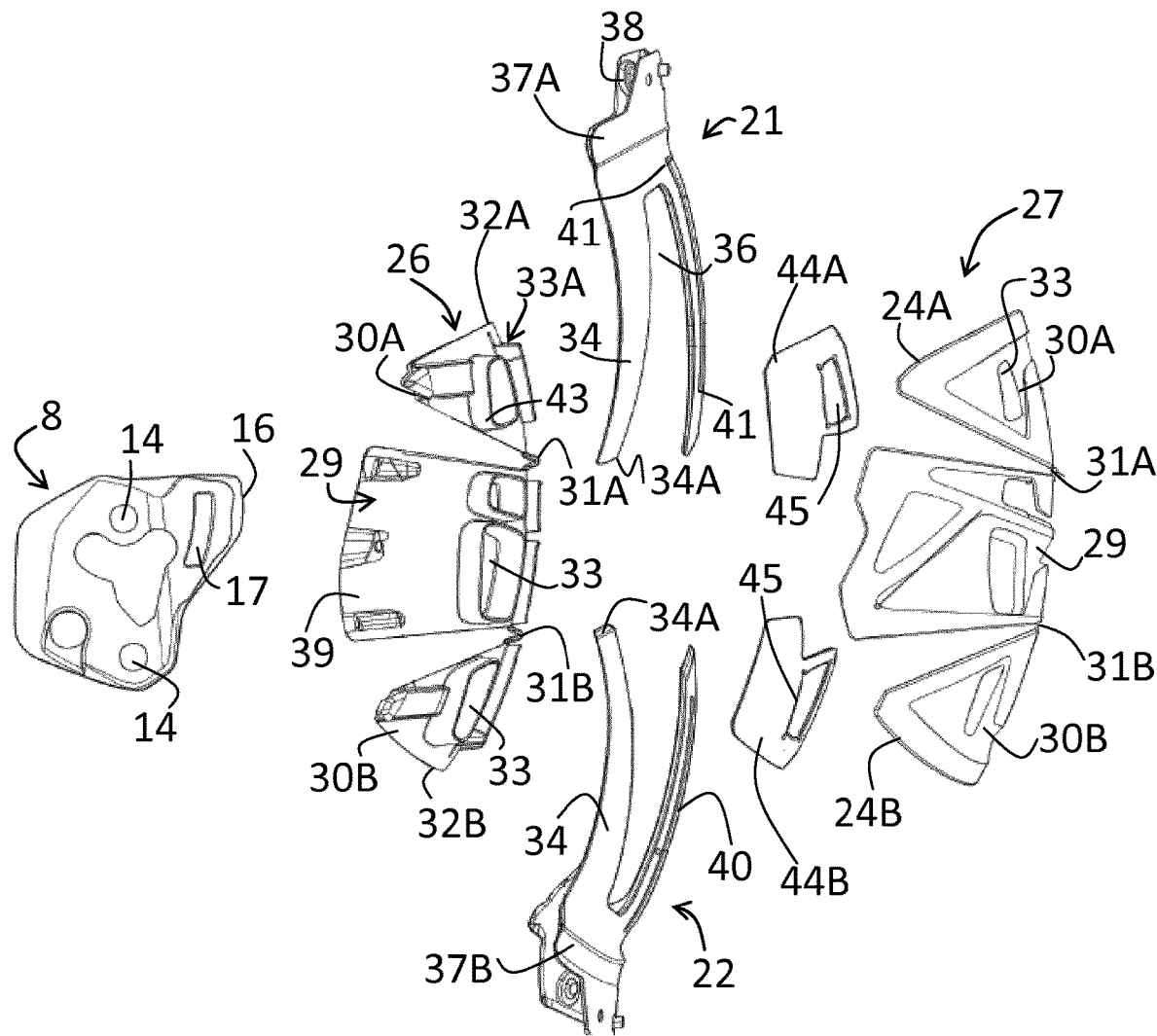
FIG. 11a shows a view similar to FIG. 11, but referring to a different embodiment.

As illustrated in FIGS. 6, 11 and 11a, there are provided a plurality of ventilation holes 33 distributed in series 33A along the portions 29, 30A, 30B of the inner shell 26 and the outer shell 27. The ventilation holes 33 of the inner shell 26 are aligned with the ventilation holes 33 of the outer shell 27.

Advantageously, the ventilation holes 33 of the inner shell 26 can have shaped walls 43 which project inside the cavity 25 when the intermediate guard member 23 is assembled and which engage the ventilation holes 33 of the outer shell 27, as shown in FIGS. 8, 9, 11 and 11a.

Preferably, each of the upper member 21 and lower member 22 comprises at least one finger-like projection 34 and the inner cavity 25 of the intermediate member 23 comprises at least one passage 35 for the slidable insertion and guidance of said at least one finger-like projection 34.

As shown in FIGS. 2-5 and 7-9, the upper member 21 and the lower member 22 can comprise a plurality of finger-like projections 34, preferably transversely staggered, while the inner cavity 25 can comprise a plurality of passages 35, also preferably transversely staggered for the insertion of a respective projection 34.

The finger-like projections 34 define longitudinal spaces 36 therebetween.

Opportunely, the upper member 21 and the lower member 22 comprise a respective connection portion 37A, 37B from which the projections 34 extent and designed to be connected to the central edge portion 6 of the respective upper frame member 4 or lower frame member 5 by suitable connection means 38, as shown in FIGS. 3 and 5.

Moreover, the finger-like projections 34 preferably have a longitudinal extension equal to the three-piece intermediate guard member 23 and may be made of a semi-rigid flexible material in order to be deformable during their sliding in the passages 35.

These latter can be formed in the cavity 25 in the spaces between the ventilation holes 33, when the inner shell 26 and the outer shell 27 are connected, in particular between the shaped walls 43, as shown in FIGS. 7-9.

In this way, the finger-like projections 34 are superimposed in the passages 35 when the upper member 21 and the lower member 22 are in the straight configuration, as shown in FIG. 3, and the ventilation holes 33 are not obstructed, because of the presence of the spaces 36 between the finger-like projections 34.

In particular, only the free ends 34A of the finger-like projections 34 are superimposed inside the passages 35 when the patella protection system 1 is the straight configuration, as shown in FIG. 3.

At the central portion 29 of the intermediate guard member 23, the shells 26, 27 and the free ends 34A of the finger-like projections 34 form a stack inside the inner cavity 25, as shown in FIG. 3, with the free ends 34A superimposed and positioned between the inner shell 26 and the outer shell 27.

Further, in the straight configuration, the finger-like projections 34 longitudinally cross the spaces between central portion 29 and the upper portion 30A and the lower portion 30B wherein the hinge sections 31A, 31B are not present.

As shown in FIGS. 1a and 11a, stabilizer wings 44A, 44B can be positioned between the inner shell 26 and the outer shell 27 at the outer sides of the hinge sections 31A, 31B so as to close the gap between the central portion 29 and the upper and lower portions 30A, 30B. The stabilizer wings 44A, 44B are preferably provided with a seat 45 designed to engage the shaped walls 43 projecting from the inner shell 26.

The stabilizer wings 44A, 44B have the function to prevent that the finger-like projections 34 during their movements can slide out from the inner cavity 25.

When the upper member 21 and the lower member 22 move to the angulated configuration, the free ends 34A of the finger-like projections 34 are not superimposed anymore but they remain inside the inner cavity 25, namely the upper 25A or the lower part 25B of the cavity 25, as shown in FIGS. 3 and 5.

In this configuration, the free ends 34A of the finger-like projections 34 are in contact with the inner surface 39, i.e. the surface facing the inner cavity 25, of the outer shell 27 and are flexed, as better shown in FIG. 5.

Advantageously, at least one of the finger-like projections 34 comprises a respective elongated slot 40 with two opposed ends 41. The slot 40 may have an extension smaller than the extension of the respective projection 34.

Accordingly, at least one of the passages 35 can comprise at least one engaging pin 42, preferably a pair of engaging pins 42, shown in FIGS. 3 and 7-10, which are slidably inserted in the slot 40. In particular, the pins 42 may be formed in the inner surfaces 39 of the upper and lower portions 30 of both the inner 26 and outer shells 27.

In this regard, the opposed ends 41 of the slot 40 define limit positions for the sliding of the pins 42 which correspond to the straight configuration or to the angulated configuration of the upper member 21 and lower member 22.

In particular, when the pins 42 of the intermediate guard member 23 abut against the end 41 of the slot 40 proximate to the connection portion 37A, 37B of the upper member 21 or the lower member 22, the patella protection system 1 is in the straight configuration. Instead, when the pins 42 abut against the end 41 of the slot 40 proximate to the free ends 34A of the finger-like projections 34, the patella protection system 1 is in the angulated configuration.

As shown in the FIGS. 2, 7-9 and 11-11a, when a plurality of finger-like projections 34 is provided, there could be provided also a plurality of slots 40 each formed on a respective finger-like projection 34. In the figures, only the central projections 34 are provided with respective slots 40. Accordingly, for each of the slots 40 a pair of pins 42 is provided and is formed in transverse staggered positions in the inner shell 26 and in the outer shell 27.

At this point of the disclosure it is clear how the predefined objects are achieved with the patella protection system and the knee brace according to the invention. As a matter of fact, the patella protection system comprises a box-like intermediate guard member which allows the insertion and guidance of the upper member and lower member. The intermediate guard member is formed by at least three pieces which could be deformed to adapt the shape of the patella protection system to the knee when it is flexed. Moreover, the outer shell of the intermediate guard member remains always exposed during the operations of the patella protection system, thus allowing for an improved absorption of the impacts against the brace. The intermediate guard member further comprises a plurality of openings which allows the breathability of the knee when the patella protection system and the brace are in use.

As an alternative, the patella protection system could also be coupled with a wearable article different from a knee brace, provided that its functioning remains the same described in the present application. For example, the protection system could be designed for protecting the wearer's elbow, or other joints which move from a straight configuration to an angulated configuration.

With regard to the embodiments of the patella protection system and the knee brace described above, the person skilled in the art may, in order to satisfy specific requirements, make modifications to and/or replace elements described with equivalent elements, without thereby departing from the scope of the accompanying claims. For example, the skilled person could replace the material of the components of the brace, or select a different type of connection between the shells, or further change the shape and the number of projections without thereby departing from the scope of the accompanying claims.

The invention claimed is:

1. A knee brace comprising:
an upper frame member for fastening to and protecting an upper part of a leg of a wearer;
a lower frame member for fastening to and protecting a lower part of the wearer's leg;
a patella protection system positioned between said upper frame member and said lower frame member;
wherein the upper frame member and the lower frame member are pivotally connected there between and with the patella protection system;
wherein said patella protection system comprises an upper member secured to the upper frame member, a lower member secured to the lower frame member, and an intermediate guard member for positioning over the patella and being operatively connected to the upper member and the lower member;
wherein said upper member and said lower member are movable within said intermediate guard member;
wherein said upper member and said lower member have a predetermined degree of overlap within the intermediate guard member when the patella protection system is in a straight configuration, the degree of overlap being reduced when the patella protection system is moved from the straight configuration to an angled configuration; and
wherein the intermediate guard member is a box-like member having an inner cavity and end openings for the slidable insertion and guidance of said upper member and said lower member.

2. The knee brace of claim 1, wherein the upper frame member and the lower frame member each comprise a pair of side brackets pivotally connected there between and about a respective rotation axis by hinge means comprising at least one stop member for limiting the rotation of said upper frame member and said lower frame member.

3. A patella protection system for a wearer comprising:
an upper member for positioning in proximity of an upper part of a leg of the wearer;
a lower member for positioning in proximity of a lower part of the wearer's leg; and
an intermediate guard member for positioning over a patella of the wearer's leg and operatively connected to the upper member and the lower member;
wherein said upper member and said lower member are movable within said intermediate guard member;
wherein said upper member and said lower member have a predetermined degree of overlap within the intermediate guard member when the patella protection system is in a straight configuration, the degree of overlap being reduced when the patella protection system is moved from the straight configuration to an angled configuration; and
wherein the intermediate guard member is a box-like member having an inner cavity and end openings for the slidable insertion and guidance of said upper member and said lower member.

4. The patella protection system of claim 3, wherein said intermediate guard member is formed by a pair of shells coupled there between and designed to delimit said inner cavity.

5. The patella protection system of claim 4, wherein each shell of the intermediate guard member comprises at least two portions connected together by at least one hinge section.

6. The patella protection system of claim 5, wherein said at least one hinge section has a reduced thickness relative to the shell portions.

7. The patella protection system of claim 6, wherein each shell comprises a central portion, an upper portion and a lower portion, said upper portion and said lower portion being connected to said central portion at a respective hinge section.

8. The patella protection system of claim 7, wherein each of said portions comprises at least one ventilation hole.

9. The patella protection system of claim 3, wherein said upper member and said lower member comprises at least one finger-like projection, and wherein said intermediate guard member comprises an inner cavity comprising at least one passage for the slidable insertion and guidance of said at least one finger-like projection.

10. The patella protection system of claim 9, wherein said upper member and said lower member comprises a plurality of finger-like projections, and wherein said inner cavity comprises a plurality of passages, each passage being designed for the slidable insertion and guidance of a respective finger-like projection.

11. The patella protection system of claim 10, wherein the finger-like projections of the upper member and the lower member are superimposed inside each of said passages when the patella protection system is in the straight configuration.

12. The patella protection system of claim 10, wherein said finger-like projections are made of a semi-rigid flexible material.

13. The patella protection system of claim 10, wherein at least one of said finger-like projections comprises an elongated slot having two opposed ends.

14. The patella protection system of claim 13, wherein at least one of said passages comprises a respective engaging pin which is slidably inserted inside said at least one slot.

15. The patella protection system of claim 14, characterized in that the opposed ends of each slot define limit positions for the sliding of said pin;
    said limit positions corresponding to the straight configuration or to the angled configuration of said upper member and said lower member.

16. The system of claim 3, wherein the patella protection system in the straight configuration has a maximum degree of overlap between said upper member and said lower member, and wherein the degree of overlap between said upper member and said lower member in the angled configuration is reduced from the maximum degree of overlap.

17. The system of claim 3, wherein when the patella protection system is moved from the straight configuration to an angled configuration, the degree of overlap can be reduced to a degree of no overlap.

18. The system of claim 3, wherein the straight configuration of the patella protection system comprises some angle of deflection from straight or parallel relationship between said upper member and said lower member, and wherein the angled configuration comprises a correspondingly larger angle of deflection between said upper member and said lower member.

19. The system of claim 3, wherein the straight configuration of the patella protection system comprises zero angle of deflection from straight or parallel relationship between said upper member and said lower member.

\* \* \* \* \*